US009801709B2

(12) United States Patent
Blum et al.

(10) Patent No.: US 9,801,709 B2
(45) Date of Patent: Oct. 31, 2017

(54) ELECTRO-ACTIVE INTRAOCULAR LENSES

(71) Applicant: e-VISION SMART OPTICS INC., Sarasota, FL (US)

(72) Inventors: Ronald Blum, Roanoke, VA (US); William Kokonaski, Gig Harbor, WA (US)

(73) Assignee: e-Vision Smart Optics, Inc., Sarasota, FL (US)

( * ) Notice: Subject to any disclaimer, the term of this patent is extended or adjusted under 35 U.S.C. 154(b) by 43 days.

(21) Appl. No.: 14/198,798

(22) Filed: Mar. 6, 2014

(65) Prior Publication Data

US 2015/0250584 A1    Sep. 10, 2015
US 2017/0209256 A9    Jul. 27, 2017

Related U.S. Application Data

(63) Continuation of application No. 11/261,035, filed on Oct. 28, 2005, now Pat. No. 8,778,022.

(60) Provisional application No. 60/692,270, filed on Jun. 21, 2005, provisional application No. 60/687,341, filed on Jun. 6, 2005, provisional application No. 60/687,342, filed on Jun. 6, 2005, provisional application No. 60/685,407, filed on May 31, 2005, provisional application No. 60/679,241, filed on May 10, 2005, provisional application No. 60/674,702, filed on Apr. 26, 2005, provisional application No. 60/673,758, filed on Apr. 22, 2005, provisional application No. 60/669,403, filed on Apr. 8, 2005, provisional application No. 60/667,094, filed on Apr. 1, 2005, provisional application No. 60/666,167, filed on Mar. 30, 2005, provisional application No.
(Continued)

(51) Int. Cl.
A61F 2/16    (2006.01)
G02C 7/08    (2006.01)

(52) U.S. Cl.
CPC ............ *A61F 2/1627* (2013.01); *G02C 7/083* (2013.01); *G02C 2202/22* (2013.01)

(58) Field of Classification Search
CPC .... A61F 2/1624; A61F 2/1627; A61F 2/1348; A61F 2/1613; A61F 2/1635; A61F 2250/0001; G02C 7/04; G02C 7/083; B29D 11/00807
See application file for complete search history.

(56) References Cited

U.S. PATENT DOCUMENTS 2,437,642 A    3/1948  Henroleau
2,576,581 A   11/1951  Edwards
(Continued)

FOREIGN PATENT DOCUMENTS

CN    ROC89113088    10/2001
CN       1466934 A    1/2004
(Continued)

OTHER PUBLICATIONS

Bertsch, A. et al., "The Sensing Contact Lens", Medical Device Technology (2006); 17: 19-21.
(Continued)

*Primary Examiner* — David H. Willse
*Assistant Examiner* — Tiffany Shipmon
(74) *Attorney, Agent, or Firm* — Cooley LLP

(57) ABSTRACT

An intraocular lens system is presented that comprises an electro-active lens comprising multiple independently controllable zones or pixels, and a controller capable of being remotely programmed.

17 Claims, 10 Drawing Sheets

Related U.S. Application Data

60/661,925, filed on Mar. 16, 2005, provisional application No. 60/659,431, filed on Mar. 9, 2005, provisional application No. 60/623,947, filed on Nov. 2, 2004, provisional application No. 60/623,946, filed on Nov. 2, 2004, provisional application No. 60/636,490, filed on Dec. 17, 2004.

(56) References Cited

U.S. PATENT DOCUMENTS

| | | |
|---|---|---|
| 3,161,718 A | 12/1964 | De Luca |
| 3,245,315 A | 4/1966 | Marks et al. |
| 3,248,460 A | 4/1966 | Naujokas |
| 3,309,162 A | 3/1967 | Kosanke et al. |
| 3,614,215 A | 10/1971 | Mackta |
| 3,738,734 A | 6/1973 | Tait et al. |
| 3,791,719 A | 2/1974 | Kratzer et al. |
| 4,062,629 A | 12/1977 | Winthrop |
| 4,174,156 A | 11/1979 | Glorieux |
| 4,181,408 A | 1/1980 | Senders |
| 4,190,330 A | 2/1980 | Berreman |
| 4,190,621 A | 2/1980 | Greshes |
| 4,264,154 A | 4/1981 | Petersen |
| 4,279,474 A | 7/1981 | Belgorod |
| 4,300,818 A | 11/1981 | Schachar |
| 4,320,939 A | 3/1982 | Mueller |
| 4,373,218 A | 2/1983 | Schachar |
| 4,395,736 A | 7/1983 | Fraleux |
| 4,418,990 A | 12/1983 | Gerber |
| 4,423,929 A | 1/1984 | Gomi |
| 4,457,585 A | 7/1984 | DuCorday |
| 4,461,550 A | 7/1984 | Legendre |
| 4,466,703 A | 8/1984 | Nishimoto |
| 4,466,706 A | 8/1984 | Lamothe, II |
| 4,529,268 A | 7/1985 | Brown |
| 4,564,267 A | 1/1986 | Nishimoto |
| 4,572,616 A | 2/1986 | Kowel et al. |
| 4,577,928 A | 3/1986 | Brown |
| 4,601,545 A | 7/1986 | Kern |
| 4,609,824 A | 9/1986 | Munier et al. |
| 4,712,870 A | 12/1987 | Robinson et al. |
| 4,756,605 A | 7/1988 | Okada et al. |
| 4,772,094 A | 9/1988 | Sheiman |
| D298,250 S | 10/1988 | Kildall |
| 4,781,440 A | 11/1988 | Toda |
| 4,787,733 A | 11/1988 | Silva |
| 4,787,903 A | 11/1988 | Grendahl |
| 4,795,248 A | 1/1989 | Okada et al. |
| 4,807,630 A | 2/1989 | Malinouskas et al. |
| 4,813,777 A | 3/1989 | Rainville et al. |
| 4,816,031 A | 3/1989 | Pfoff |
| 4,818,095 A | 4/1989 | Takeuchi |
| 4,836,652 A | 6/1989 | Oishi et al. |
| 4,842,400 A | 6/1989 | Klein |
| 4,869,588 A | 9/1989 | Frieder et al. |
| 4,873,029 A | 10/1989 | Blum |
| 4,880,300 A | 11/1989 | Payner et al. |
| 4,890,903 A | 1/1990 | Treisman et al. |
| 4,904,063 A | 2/1990 | Okada et al. |
| 4,907,860 A | 3/1990 | Noble |
| 4,909,626 A | 3/1990 | Purvis et al. |
| 4,919,520 A | 4/1990 | Okada et al. |
| 4,921,728 A | 5/1990 | Takiguchi |
| 4,927,241 A | 5/1990 | Kuijk |
| 4,929,865 A | 5/1990 | Blum |
| 4,930,884 A | 6/1990 | Tichenor et al. |
| 4,944,584 A | 7/1990 | Maeda et al. |
| 4,945,242 A | 7/1990 | Berger et al. |
| 4,952,048 A | 8/1990 | Frieder et al. |
| 4,952,788 A | 8/1990 | Berger et al. |
| 4,955,712 A | 9/1990 | Barth et al. |
| 4,958,907 A | 9/1990 | Davis |
| 4,961,639 A | 10/1990 | Lazarus |
| 4,968,127 A | 11/1990 | Russell et al. |
| 4,981,342 A | 1/1991 | Fiala |
| 4,991,951 A | 2/1991 | Mizuno et al. |
| 5,015,086 A | 5/1991 | Okaue et al. |
| 5,030,882 A | 7/1991 | Solero |
| 5,050,981 A | 9/1991 | Roffman |
| 5,066,301 A | 11/1991 | Wiley |
| 5,067,795 A | 11/1991 | Senatore |
| 5,073,021 A | 12/1991 | Marron |
| 5,076,665 A | 12/1991 | Petersen |
| 5,089,023 A | 2/1992 | Swanson |
| 5,091,801 A | 2/1992 | Ebstein |
| 5,108,169 A | 4/1992 | Mandell |
| 5,114,628 A | 5/1992 | Hofer et al. |
| 5,122,974 A | 6/1992 | Chance et al. |
| 5,130,856 A | 7/1992 | Tichenor et al. |
| 5,142,411 A | 8/1992 | Fiala |
| 5,147,585 A | 9/1992 | Blum |
| 5,150,234 A | 9/1992 | Takahashi et al. |
| 5,171,266 A | 12/1992 | Wiley et al. |
| 5,173,723 A | 12/1992 | Volk |
| 5,178,800 A | 1/1993 | Blum |
| 5,182,585 A | 1/1993 | Stoner |
| 5,184,156 A | 2/1993 | Black et al. |
| 5,200,859 A | 4/1993 | Payner et al. |
| 5,208,688 A | 5/1993 | Fergason et al. |
| 5,219,497 A | 6/1993 | Blum |
| 5,229,797 A | 7/1993 | Futhey et al. |
| 5,229,885 A | 7/1993 | Quaglia |
| 5,231,430 A | 7/1993 | Kohayakawa |
| 5,239,412 A | 8/1993 | Naka et al. |
| D342,063 S | 12/1993 | Howitt et al. |
| 5,305,028 A | 4/1994 | Okano |
| 5,306,926 A | 4/1994 | Yonemoto |
| 5,324,930 A | 6/1994 | Jech, Jr. |
| D350,342 S | 9/1994 | Sack |
| 5,352,886 A | 10/1994 | Kane |
| 5,359,444 A | 10/1994 | Piosenka et al. |
| 5,375,006 A | 12/1994 | Haas |
| 5,382,986 A | 1/1995 | Black et al. |
| 5,386,308 A | 1/1995 | Michel et al. |
| 5,411,537 A | 5/1995 | Munshi et al. |
| 5,424,927 A | 6/1995 | Schaller et al. |
| 5,440,357 A | 8/1995 | Quaglia |
| 5,443,506 A | 8/1995 | Garabet |
| 5,451,766 A | 9/1995 | Van Berkel |
| 5,488,439 A | 1/1996 | Weltmann |
| 5,512,371 A | 4/1996 | Gupta et al. |
| 5,522,323 A | 6/1996 | Richard |
| 5,552,841 A | 9/1996 | Gallorini et al. |
| 5,608,587 A | 3/1997 | Smith |
| 5,615,588 A | 4/1997 | Gottschald |
| 5,653,751 A | 8/1997 | Samiy et al. |
| 5,654,786 A | 8/1997 | Bylander |
| 5,668,620 A | 9/1997 | Kurtin et al. |
| 5,682,223 A | 10/1997 | Menezes et al. |
| 5,683,457 A | 11/1997 | Gupta et al. |
| RE35,691 E | 12/1997 | Theirl et al. |
| 5,702,819 A | 12/1997 | Gupta et al. |
| 5,712,721 A | 1/1998 | Large |
| 5,728,155 A | 3/1998 | Anello et al. |
| 5,728,156 A | 3/1998 | Gupta et al. |
| 5,739,959 A | 4/1998 | Quaglia |
| 5,757,458 A | 5/1998 | Miller et al. |
| 5,774,213 A | 6/1998 | Trebino et al. |
| 5,777,719 A | 7/1998 | Williams et al. |
| 5,815,233 A | 9/1998 | Morokawa et al. |
| 5,815,239 A | 9/1998 | Chapman et al. |
| 5,821,536 A | 10/1998 | Pettit |
| 5,859,685 A | 1/1999 | Gupta et al. |
| 5,861,934 A | 1/1999 | Blum et al. |
| 5,861,936 A | 1/1999 | Sorensen |
| 5,877,876 A | 3/1999 | Birdwell |
| 5,900,720 A | 5/1999 | Kallman et al. |
| 5,905,561 A | 5/1999 | Lee et al. |
| 5,913,815 A | 6/1999 | Ball et al. |
| 5,949,521 A | 9/1999 | Williams et al. |
| 5,953,098 A | 9/1999 | Lieberman et al. |
| 5,956,183 A | 9/1999 | Epstein et al. |
| 5,963,300 A | 10/1999 | Horwitz |
| 5,971,540 A | 10/1999 | Ofner |

(56) References Cited

U.S. PATENT DOCUMENTS

| | | |
|---|---|---|
| 5,980,037 A | 11/1999 | Conway |
| 5,999,328 A | 12/1999 | Kurtin et al. |
| 6,040,947 A | 3/2000 | Kurtin et al. |
| 6,050,687 A | 4/2000 | Bille et al. |
| 6,069,742 A | 5/2000 | Silver |
| 6,086,203 A | 7/2000 | Blum et al. |
| 6,086,204 A | 7/2000 | Magnante |
| 6,095,651 A | 8/2000 | Williams et al. |
| 6,099,117 A | 8/2000 | Gregory |
| 6,115,177 A | 9/2000 | Vossler |
| 6,139,148 A | 10/2000 | Menezes |
| 6,145,987 A | 11/2000 | Baude et al. |
| 6,188,525 B1 | 2/2001 | Silver |
| 6,191,881 B1 | 2/2001 | Tajima |
| 6,197,057 B1 | 3/2001 | Peyman et al. |
| 6,199,984 B1 | 3/2001 | Menezes |
| 6,199,986 B1 | 3/2001 | Williams et al. |
| 6,213,602 B1 | 4/2001 | Smarto |
| 6,270,220 B1 | 8/2001 | Keren |
| 6,271,915 B1 | 8/2001 | Frey et al. |
| 6,282,449 B1 | 8/2001 | Kamerling et al. |
| 6,299,311 B1 | 10/2001 | Williams et al. |
| 6,305,802 B1 | 10/2001 | Roffman et al. |
| 6,325,508 B1 | 12/2001 | Decreton et al. |
| 6,338,559 B1 | 1/2002 | Williams et al. |
| 6,350,031 B1 | 2/2002 | Lashkari et al. |
| 6,358,281 B1 | 3/2002 | Berrang et al. |
| 6,390,623 B1 | 5/2002 | Kokonaski et al. |
| 6,396,622 B1 | 5/2002 | Alden |
| 6,437,762 B1 | 8/2002 | Birdwell |
| 6,437,925 B1 | 8/2002 | Nishioka |
| 6,464,363 B1 | 10/2002 | Nishioka et al. |
| 6,491,394 B1 | 12/2002 | Blum et al. |
| 6,501,443 B1 | 12/2002 | McMahon |
| 6,554,425 B1 | 4/2003 | Roffman et al. |
| 6,569,199 B1 | 5/2003 | Dotan et al. |
| 6,609,794 B2 | 8/2003 | Levine |
| 6,614,408 B1 | 9/2003 | Mann |
| 6,616,275 B1 | 9/2003 | Dick et al. |
| 6,616,279 B1 | 9/2003 | Davis et al. |
| 6,618,208 B1 | 9/2003 | Silver |
| 6,626,532 B1 | 9/2003 | Nishioka et al. |
| 6,631,001 B2 | 10/2003 | Kuiseko |
| 6,638,304 B2 | 10/2003 | Azar |
| 6,643,552 B2 | 11/2003 | Edell et al. |
| 6,652,096 B1 | 11/2003 | Morris et al. |
| 6,667,471 B2 | 12/2003 | Bos et al. |
| 6,682,195 B2 | 1/2004 | Dreher |
| 6,705,729 B2 | 3/2004 | Piers et al. |
| 6,709,105 B2 | 3/2004 | Menezes |
| 6,709,107 B2 | 3/2004 | Jiang et al. |
| 6,709,108 B2 | 3/2004 | Levine et al. |
| 6,918,570 B2 | 3/2004 | Blum et al. |
| 6,738,199 B2 | 5/2004 | Nishioka |
| 6,743,337 B1 | 6/2004 | Ischdonat |
| 6,768,536 B2 | 7/2004 | Okuwaki et al. |
| 6,774,871 B2 | 8/2004 | Birdwell |
| 6,778,246 B2 | 8/2004 | Sun et al. |
| 6,793,340 B1 | 9/2004 | Morris et al. |
| 6,833,938 B2 | 12/2004 | Nishioka |
| 6,840,619 B2 | 1/2005 | Dreher |
| 6,851,805 B2 | 2/2005 | Blum et al. |
| 6,857,741 B2 | 2/2005 | Blum et al. |
| 6,859,333 B1 | 2/2005 | Ren et al. |
| 6,871,951 B2 | 3/2005 | Blum et al. |
| 6,883,916 B2 | 4/2005 | Menezes |
| 6,886,938 B1 | 5/2005 | Menezes |
| 6,893,124 B1 | 5/2005 | Kurtin |
| 6,894,751 B2 | 5/2005 | Payne et al. |
| 6,902,271 B2 | 6/2005 | Perrott et al. |
| 6,918,670 B2 | 7/2005 | Blum et al. |
| 6,948,818 B2 | 9/2005 | Williams et al. |
| 6,951,391 B2 | 10/2005 | Morris et al. |
| 6,955,433 B1 | 10/2005 | Wooley et al. |
| 6,956,682 B2 | 10/2005 | Wooley |
| 6,976,982 B2 | 12/2005 | Santini et al. |
| 6,986,579 B2 | 1/2006 | Blum et al. |
| 7,008,054 B1 | 3/2006 | Kurtin et al. |
| 7,009,757 B2 | 3/2006 | Nishioka et al. |
| 7,019,890 B2 | 3/2006 | Meredith et al. |
| 7,041,133 B1 | 5/2006 | Azar |
| 7,085,065 B2 | 8/2006 | Silver |
| 7,133,172 B2 | 11/2006 | Nishioka |
| 7,137,702 B2 | 11/2006 | Piers et al. |
| 7,137,952 B2 | 11/2006 | Leonardi et al. |
| 7,159,981 B2 | 1/2007 | Kato |
| 7,159,983 B2 | 1/2007 | Menezes et al. |
| 7,188,948 B2 | 3/2007 | Blum et al. |
| 7,195,353 B2 | 3/2007 | Blum et al. |
| 7,209,097 B2 | 4/2007 | Suyama |
| 7,229,173 B2 | 6/2007 | Menezes et al. |
| 7,261,736 B1 | 8/2007 | Azar |
| 7,290,876 B2 | 11/2007 | Duston et al. |
| 7,396,126 B2 | 7/2008 | Blum et al. |
| 7,404,636 B2 | 7/2008 | Blum et al. |
| 7,475,984 B2 | 1/2009 | Blum et al. |
| 7,926,940 B2 | 4/2011 | Blum et al. |
| 2001/0055094 A1 | 12/2001 | Zhang |
| 2002/0038134 A1 | 3/2002 | Greenberg et al. |
| 2002/0140899 A1 | 10/2002 | Blum et al. |
| 2002/0149739 A1 | 10/2002 | Perrott et al. |
| 2002/0186346 A1 | 12/2002 | Stantz et al. |
| 2003/0004546 A1 | 1/2003 | Casey |
| 2003/0018383 A1 | 1/2003 | Azar |
| 2003/0112523 A1 | 6/2003 | Daniell |
| 2003/0151721 A1 | 8/2003 | Lai et al. |
| 2003/0199978 A1 | 10/2003 | Lindsey et al. |
| 2003/0208265 A1 | 11/2003 | Ho et al. |
| 2003/0210377 A1 | 11/2003 | Blum et al. |
| 2004/0008319 A1 | 1/2004 | Lai et al. |
| 2004/0010310 A1 | 1/2004 | Peyman |
| 2004/0039298 A1 | 2/2004 | Abreu |
| 2004/0102843 A1 | 5/2004 | Yagi |
| 2004/0108971 A1 | 6/2004 | Waldern et al. |
| 2004/0117011 A1 | 6/2004 | Aharoni et al. |
| 2004/0130677 A1 | 7/2004 | Liang et al. |
| 2004/0179280 A1 | 9/2004 | Nishioka |
| 2004/0186533 A1 | 9/2004 | Greenberg et al. |
| 2004/0196435 A1 | 10/2004 | Dick et al. |
| 2004/0212804 A1 | 10/2004 | Neff et al. |
| 2004/0246440 A1 | 12/2004 | Andino et al. |
| 2004/0260520 A1 | 12/2004 | Braendle et al. |
| 2005/0073739 A1 | 4/2005 | Meredith et al. |
| 2005/0099594 A1 | 5/2005 | Blum et al. |
| 2005/0113912 A1 | 5/2005 | Feenstra et al. |
| 2005/0124983 A1 | 6/2005 | Frey et al. |
| 2005/0222624 A1 | 10/2005 | Greenberg et al. |
| 2005/0237485 A1 | 10/2005 | Blum et al. |
| 2005/0256571 A1 | 11/2005 | Azar |
| 2006/0036295 A1 | 2/2006 | Greenberg et al. |
| 2006/0044510 A1 | 3/2006 | Williams et al. |
| 2006/0095128 A1 | 5/2006 | Blum et al. |
| 2006/0113054 A1 | 6/2006 | Silvestrini |
| 2006/0122531 A1 | 6/2006 | Goodall et al. |
| 2006/0164593 A1 | 7/2006 | Peyghambarian |
| 2006/0183986 A1 | 8/2006 | Rice et al. |
| 2007/0198083 A1 | 8/2007 | Sel et al. |
| 2009/0033863 A1 | 2/2009 | Blum et al. |
| 2009/0204207 A1 | 8/2009 | Blum et al. |
| 2009/0221907 A1 | 9/2009 | Bar-Tal |
| 2011/0152969 A1 | 6/2011 | Zehnder et al. |

FOREIGN PATENT DOCUMENTS

| | | |
|---|---|---|
| DE | 4223395 A1 | 1/1994 |
| EP | 0154962 A2 | 9/1985 |
| EP | 0233104 A1 | 8/1987 |
| EP | 0237365 A1 | 9/1987 |
| EP | 0 319158 A1 | 6/1989 |
| EP | 0578833 A1 | 1/1994 |
| EP | 0649044 B1 | 4/1995 |
| EP | 0 918 248 A2 | 5/1999 |
| EP | 0918248 | 5/1999 |
| EP | 1 491 877 A1 | 12/2004 |

(56) References Cited

FOREIGN PATENT DOCUMENTS

| | | |
|---|---|---|
| EP | 1 762 269 A2 | 3/2007 |
| GB | 2169417 A | 7/1986 |
| GB | 2170613 A | 8/1986 |
| GB | 2370509 A | 7/2002 |
| HK | 1122719 A | 5/2009 |
| JP | 55-076323 A | 6/1980 |
| JP | 61156227 A | 7/1986 |
| JP | 61-502221 | 10/1986 |
| JP | S63-57044 A | 3/1988 |
| JP | 01-237610 A2 | 9/1989 |
| JP | 05-100201 A | 4/1993 |
| JP | 7028002 A | 1/1995 |
| JP | H08-508826 | 9/1996 |
| JP | 11352445 A | 12/1999 |
| JP | 2002-533158 | 10/2002 |
| JP | 2003-512889 | 4/2003 |
| JP | 2003-230590 A | 8/2003 |
| JP | 2007-508875 A | 4/2007 |
| JP | 2007-323062 A | 12/2007 |
| JP | 08-0508826 | 3/2008 |
| JP | 2008-539422 A | 11/2008 |
| WO | WO 92/01417 A1 | 2/1992 |
| WO | WO 93/21010 A1 | 10/1993 |
| WO | WO 94/23334 A1 | 10/1994 |
| WO | WO 97/06751 | 2/1997 |
| WO | WO 98/27863 A1 | 7/1998 |
| WO | WO 99/27334 A1 | 6/1999 |
| WO | WO 00/38593 A1 | 7/2000 |
| WO | WO 02/080828 A1 | 10/2002 |
| WO | WO 03/007851 | 1/2003 |
| WO | WO 03/037111 A1 | 5/2003 |
| WO | WO 03/050472 A1 | 6/2003 |
| WO | WO 03/068059 A2 | 8/2003 |
| WO | WO 2004/008189 A1 | 1/2004 |
| WO | WO 2004/015460 | 2/2004 |
| WO | WO 2004/015481 A1 | 2/2004 |
| WO | WO 2004/034095 A2 | 4/2004 |
| WO | WO 2004/072687 A2 | 8/2004 |
| WO | WO 85/05466 A1 | 12/2005 |
| WO | WO 2006/015913 A1 | 2/2006 |
| WO | WO 2006/050171 A2 | 5/2006 |
| WO | WO 2006/118619 A1 | 11/2006 |
| WO | WO 2007/006376 A2 | 1/2007 |
| WO | WO 2009/115102 A1 | 9/2009 |

OTHER PUBLICATIONS

Eggers, T. et al., "Wireless Intra-ocular Pressure Monitoring System Integrated in an Artificial Lens", Presented at the First Annual International IEEE-EMBS Special Topic Conference on Microtechnologies in Medicine & Biology, Lyon, France, Oct. 12-14, 2000; Paper 7: 466-469.

Leonardi, M. et al., "A Soft Contact Lens with a MEMS Strain Gage Embedded for Intraocular Pressure Monitoring", Transducers '03; The 12th International Conference on Solid Slate Sensors, Actuators and Microsyslems, Boston, Jun. 8-12, 2003; 3B2.5: 1043-1046.

Leonardi, M. et al., "First Steps toward Noninvasive IOP—Monitoring with a Sensing Contact Lens", Investigative Ophthalmology & Visual Science (2004); 45(9): 3113-3117.

Pitchon, E.M. et al., "First In-Vivo Human Monitoring of Intraocular Pressure Fluctuation and Ocular Pulsation by a Wireless Soft Contact Lens Sensor." Congress of the European Glaucoma Society, Berlin, Jun. 2008; Congres annuel de la Societe francaise d'ophtalmologie, Paris, May 2008; ARVO Meeting (The Association for Research in Vision and Ophthalmology), Apr. 27-May 1, 2008, Fort Lauderdale American Glaucoma Society, 18th Annual Meeting, Mar. 2008, Washington, 1 page.

Walter, P. et al., "Development of a completely encapsulated intraocular pressure sensor", Ophthalmic Research (2000); 32: 278-284.

Final Office Action for U.S. Appl. No. 12/465,970 dated Nov. 8, 2012.

Supplementary European Search Report of Application No. EP 05824718 issued Nov. 19, 2007.

International Search Report of Application No. PCT/US05/39101 mailed on Jul. 7, 2006.

International Search Report of Application No. PCT/US08/51649 mailed on Jul. 7, 2008.

International Search Report for PCT/US2009/044168 dated Oct. 7, 2009.

International Preliminary Report on Patentability for Application No. PCT/US2005/039101 dated May 8, 2007.

International Preliminary Report on Patentability for PCT/US2009/044168 dated Nov. 17, 2010.

Danfield, C., Phakic Intraocular Lens Implant, WordcatTop Quality Articles, 2 pages, Retrieved from the Internet on Nov. 20, 2008: http://www.wordcat.co.uk/articles/phakic-intraocular-lens-implant/279/.

Anderson, M., "Adaptive Optics: Liquid Crystals Lower the Cost of Adaptive Optics" Laser Focus World (1999): 1-3.

Bradley, Arthur, "Profile: Larry N. Thibos, PhD., and Donald T. Miller, PhD." Indian Journal of Optometry; 2:1 (Spring 1999).

Davis, Robert A., "Computer Vision Syndrome—The Eyestrain Epidemic" Review of Optometry (Sep. 15, 1997).

Eyecare Business (Oct. 1997), 76 pages.

Kowel et al "Focusing by electrical modulation of refraction in a liquid crystal cell" *Applied Optic*, 23(2): 278-289 (1984).

Lazarus, S.M., "The Use of Yoked Base-Up and Base-In Prism for Reducing Eye Strain at the Computer." Journal of the American Optometric Association, 67.4: 204-208 (1996).

Miller et al., "Requirements for the segmented spatial light modulators for diffraction-limited imaging through aberrated eyes," G.D. Love, ed. Proceedings of the 2nd International Workshop on Adaptive Optics for Industry and Medicine, World Scientific, Singapore, 63-68 (Jul. 1999).

Naumov et al., "Control Optimization of Spherical Modal Liquid Crystal Lenses", Optics Express, 4(9): 344-352 (1999).

Naumov et al., "Liquid Crystal Adaptive Lenses with Modal Control" Optics Letters, 23(13): 992-994 (1998).

Optics, Org, Dec. 19, 2006 "Liquid Lenses Eye Commercial Breakthrough" Opto & Laser Europe (Nov. 2003), 4 pages.

Tarascon and Armand, "Issues and challenges facing rechargeable lithium batteries" *Nature*, 414:359-367 (2001).

Thibos, Larry N., et al. "Use of Liquid-Crystal Adaptive-Optice to Alter the Refractive State of the Eye; Optometry and Vision Science", 74.7 : 581-587.

Thibos, Larry N., et al. "Vision through a liquid-crystal spatial light modulator" *Adaptive Optics Conference*; Durham, UK (1999).

Thibos and Miller, "Electronic Spectacles for the 21 Century" Indian Journal of Optometry, 2(1): 6-10 (Spring 1999).

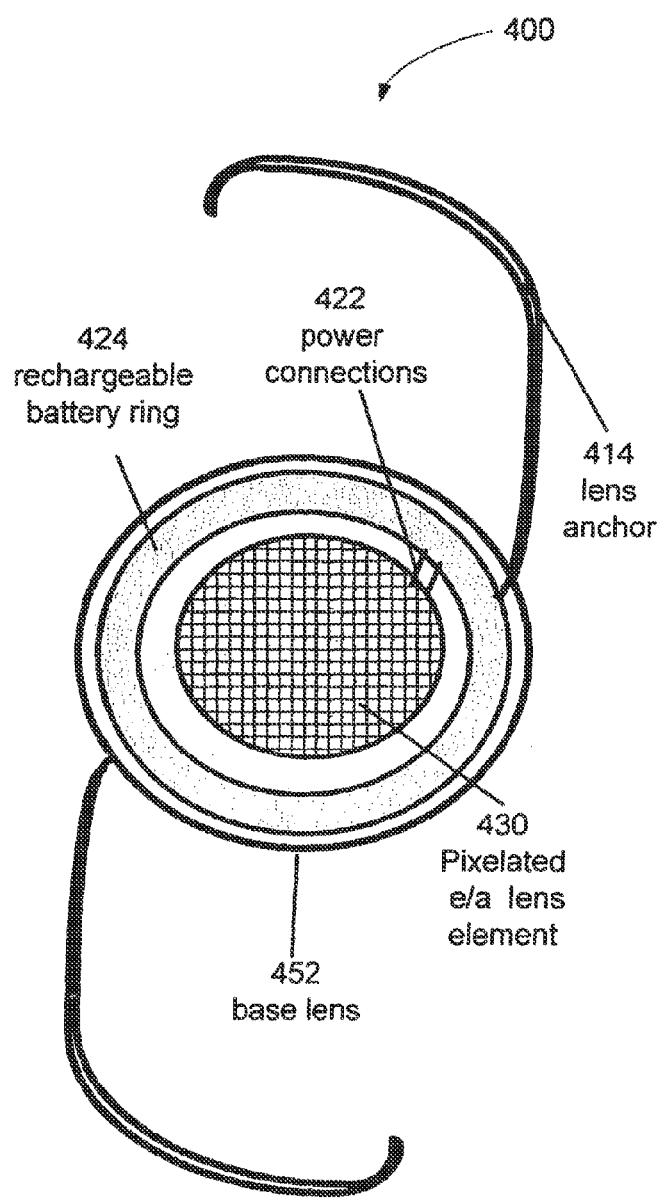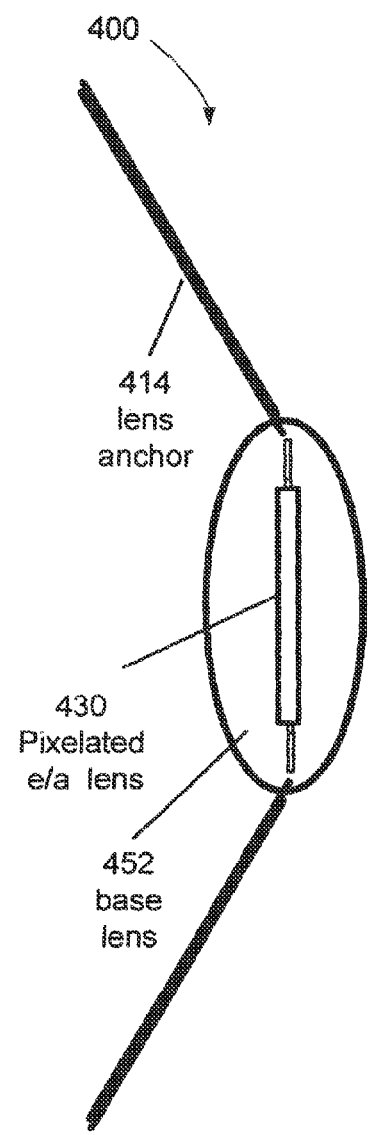
Figure 4A
Figure 4B

US 9,801,709 B2

ELECTRO-ACTIVE INTRAOCULAR LENSES

RELATED PATENTS AND APPLICATIONS

This application is a continuation under 35 U.S.C. §120 of U.S. application Ser. No. 11/261,035, now U.S. Pat. No. 8,778,022, which was filed on Oct. 2, 2005, and which in turn claims the benefit under 35 U.S.C. §119(e) of: U.S. application No. 60/692,270, filed Jun. 21, 2005; U.S. application No. 60/687,341, filed Jun. 6, 2005; U.S. application No. 60/687,342, filed Jun. 6, 2005; U.S. application No. 60/685,407, filed May 31, 2005; U.S. application No. 60/679,241, filed May 10, 2005; U.S. application No. 60/674,702, filed Apr. 26, 2005; U.S. application No. 60/673,758, filed Apr. 22, 2005; U.S. application No. 60/669,403, filed Apr. 8, 2005; U.S. application No. 60/667,094, filed Apr. 1, 2005; U.S. application No. 60/666,167, filed Mar. 30, 2005; U.S. application No. 60/661,925, filed Mar. 16, 2005; U.S. application No. 60/659,431, filed Mar. 9, 2005; U.S. application No. 60/636,490, filed Dec. 17, 2004; U.S. application No. 60/623,947, filed Nov. 2, 2004; and U.S. application No. 60/623,946, filed Nov. 2, 2004, each of which is incorporated herein by reference in its entirety.

The following applications, provisional applications, and patents are incorporated by reference in their entirety: U.S. application Ser. No. 11/232,551 filed Sep. 22, 2005; U.S. Pat. No. 6,918,670 issued Jul. 19, 2005; U.S. application Ser. No. 11/183,454 filed Jul. 18, 2005; U.S. Provisional Application No. 60/692,270 filed Jul. 21, 2005; U.S. Provisional Application No. 60/687,342 filed Jun. 6, 2005; U.S. Provisional Application No. 60/687,341 filed Jun. 6, 2005; U.S. Provisional Application No. 60/685,407 filed May 31, 2005; U.S. Provisional Application No. 60/679,241 filed May 10, 2005; U.S. Provisional Application No. 60/674,702 filed Apr. 26, 2005; U.S. Provisional Application No. 60/673,758 filed Apr. 22, 2005; U.S. application Ser. No. 11/109,360 filed Apr. 19, 2005; U.S. Provisional Application No. 60/669,403 filed Apr. 8, 2005; U.S. Provisional Application No. 60/667,094 filed Apr. 1, 2005; U.S. Provisional Application No. 60/666,167 filed Mar. 30, 2005; U.S. Pat. No. 6,871,951 issued Mar. 29, 2005; U.S. application Ser. No. 11/091,104 filed Mar. 28, 2005; U.S. Provisional Application No. 60/661,925 filed Mar. 16, 2005; U.S. Provisional Application No. 60/659,431 filed Mar. 9, 2005; U.S. application Ser. No. 11/063,323 filed Feb. 22, 2005; U.S. Pat. No. 6,857,741 issued Feb. 22, 2005; U.S. Pat. No. 6,851,805 issued Feb. 8, 2005; U.S. application Ser. No. 11/036,501 filed Jan. 14, 2005; U.S. application Ser. No. 11/030,690 filed Jan. 6, 2005; U.S. application Ser. No. 10/996,781 filed Nov. 24, 2004; U.S. Provisional Application No. 60/623,947 filed Nov. 2, 2004; U.S. application Ser. No. 10/924,619 filed Aug. 24, 2004; U.S. application Ser. No. 10/918,496 filed Aug. 13, 2004; U.S. application Ser. No. 10/863,949 filed Jun. 9, 2004; U.S. Pat. No. 6,733,130 issued May 11, 2004; U.S. application Ser. No. 10/772,917 filed Feb. 5, 2004; U.S. Pat. No. 6,619,799 issued Sep. 16, 2003; U.S. application Ser. No. 10/664,112 filed Aug. 20, 2003; U.S. application Ser. No. 10/627,828 filed Jul. 25, 2003; U.S. application Ser. No. 10/387,143 filed Mar. 12, 2003; U.S. Pat. No. 6,517,203 issued Feb. 11, 2003; U.S. Pat. No. 6,491,391 issue Dec. 10, 2002; U.S. Pat. No. 6,491,394 issued Dec. 10, 2002; and U.S. application Ser. No. 10/263,707 filed Oct. 4, 2002.

BACKGROUND

The present invention relates to field of Intraocular Lenses (IOLs). In particular, the present invention relates to Intraocular Lenses wherein an electro-active element provides at least a portion of the IOL's refractive power, or prismatic power, or at least a portion of the tinting.

Intraocular lenses (IOLs) are typically permanent, plastic lenses that are surgically implanted inside of the eyeball to replace or supplement the eye's natural crystalline lens. They have been used in the United States since the late 1960s to restore vision to cataract patients, and more recently are being used in several types of refractive eye surgery.

The natural crystalline lens is critical component of the complex optical system of the eye. The crystalline lens provides about 17 diopters of the total 60 diopters of the refractive power of a healthy eye. Further, a healthy crystalline lens provides adjustable focusing when deformed by the muscular ciliary body that circumferentially surrounds the crystalline lens. As the eye ages, the flexibility of the crystalline lens decreases and this adjustable focusing is diminished. Thus, this critical crystalline lens almost invariably loses flexibility with age, and often loses transparency with age due to cataracts or other diseases.

Most intraocular lenses used in cataract surgery may be folded and inserted through the same tiny opening that was used to remove the natural crystalline lens. Once in the eye, the lens may unfold to its full size. The opening in the eye is so small that it heals itself quickly without stitches. The intraocular lenses may be made of inert materials that do not trigger rejection responses by the body.

In most cases, IOLs are permanent. They rarely need replacement, except in the instances where the measurements of the eye prior to surgery have not accurately determined the required focusing power of the IOL. Also, the surgery itself may change the optical characteristics of the eye. In most cases, the intraocular lenses implanted during cataract surgery are monofocal lenses, and the optical power of the IOL is selected such that the power of the eye is set for distance vision. Therefore, in most cases the patient will still require reading glasses after surgery. Intraocular lens implants may be static multifocal lenses, which attempt to function more like the eye's natural lens by providing clear vision at a distance and reasonable focus for a range of near distances, for patients with presbyopia. Not all patients are good candidates for the multifocal lens; however, those who can use the lens are some what pleased with the results.

More recently, accommodative IOLs have been introduced. These accommodative IOLs actually change focus by movement (physically deforming and/or translating within the orbit of the eye) as the muscular ciliary body reacts to an accommodative stimulus from the brain, similar to the way the natural crystalline lens focuses. While these offer promise, accommodative IOLs still have not been perfected. In spite of these limited successes, the multifocal IOL and present accommodative IOLs still have a substantial decrease in performance when compared to a healthy natural crystalline lens.

Another ocular lens that holds promise for correcting presbyopia is the Small Diameter Corneal Inlay (SDCI). The Small Diameter Corneal Inlay (SDCI) is a prescription lens that is inserted into the corneal tissue to create an effect similar to a bifocal contact lens. Corneal Inlays (SDCI) are early in their development and it is still too early to understand how well they will function and also how effective they will become.

While all these emerging surgical procedures have their merits, they all have a substantial decrease in performance when compared to a young healthy natural crystalline lens. The present invention addresses these shortcomings by providing an intraocular lens that behaves in a manner similar to the natural crystalline lens.

SUMMARY

An illustrative aspect of the invention provides an intraocular lens system comprising an electro-active lens comprising multiple independently controllable zones or pixels, and a controller capable of being remotely programmed.

Other aspects of the invention will become apparent from the following descriptions taken in conjunction with the following drawings, although variations and modifications may be effected without departing from the spirit and scope of the novel concepts of the disclosure.

BRIEF DESCRIPTION OF THE DRAWINGS

The present invention can be more fully understood by reading the following detailed description together with the accompanying drawings, in which like reference indicators are used to designate like elements.

FIG. 4A displays a front view of an intraocular lens embodiment with a pixelated electro-active lens and a rechargeable battery ring.

FIG. 4B displays amide view of an intraocular lens embodiment with a pixelated electro-active lens and a rechargeable battery ring.

DETAILED DESCRIPTION

Figure 1:
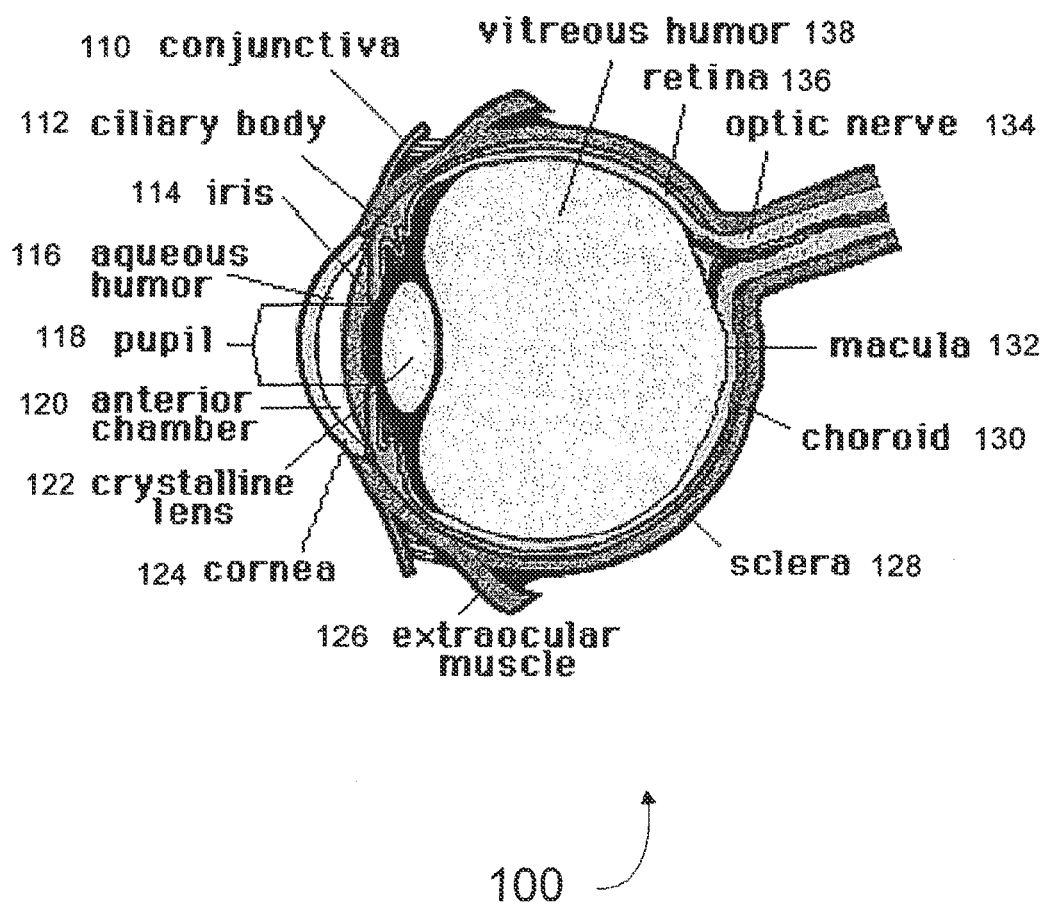
FIG. 1 displays the major anatomical components of a human eye.

Hereinafter, various embodiments of the invention will be described. As used herein, any term in the singular may be interpreted in the plural, and alternately, any term in the plural may be interpreted to be in the singular.

Electro-active materials comprise optical properties that may be varied by electrical control. For example, transmission of light may be controlled to produce tinting or a sunglass effect. Further, the index of refraction may be electrically controlled to produce focusing and or prismatic effects. One class of electro-active material is liquid crystals. Liquid crystals comprise a state of aggregation that is intermediate between the crystalline solid and the amorphous liquid. The properties of liquid crystals may be controlled electrically, thermally, or chemically. Many liquid crystals are composed of rod-like molecules, and classified broadly as: nematic, cholesteric, and smectic.

There are several characteristics of electro-active materials which are useful in IOLs. First, the optical characteristics may be generated by thin layers (rather than by the curvature of conventional lenses which may require thick lenses). These thin layers may be placed in locations where it may be difficult to place conventional lenses, for example in the anterior chamber of the eye (between the iris and the crystalline lens). In addition, it is possible to stack (place in series optically) the electro-active layers in such a manner as to get an additive effect for the overall optical power created, including prism, conventional refractive error, or higher order aberration correction, in a thin structure that may be placed in either the anterior or the posterior chamber of the eye.

Second, the optical characteristics may be actively controlled. For example, an electro-active lens may designed to become darker (more tinted, and transmit less light) under bright light conditions. This tinting may be generated automatically by measuring the brightness using, for example, a photodiode or solar cell. Alternately, the tinting may be controlled by the decisions of the user by way of a remote control.

Similarly, the focus of an electro-active lens may be controlled electrically. The focus may be controlled automatically using, for example, a range finder, or a tilt meter, or triangulation based on the direction of both eyes, the forces exerted on the lens by the muscles of the eye. Alternately, the focus may be controlled by the decisions of the user by way of a remote control.

Third, electrical control creates the potential for correcting complex and high order visual defects. Conventional intraocular lenses are limited to addressing certain visual defects for various manufacturing reasons. However, an electro-active lens with a large number of individually addressable controlled small elements (for example, an array of very small pixels) may address very complex and high order visual defects. Further, the control may be simplified by creating individually addressable elements in arbitrary configurations, such as a series of concentric circles, or a series of approximately concentric ellipsis, or whatever customized configuration efficiently corrects the visual defect. The design, manufacture, and control of an array of small pixels has similarities with the manufacture of Liquid Crystal Displays (LCDs). Correction of complex visual defects such as higher order aberrations of the eye creates the possibility of "superhuman" visual acuity, wherein the vision is not limited by the lenses (either biological or corrective), but rather is limited by the inherent anatomy and physics of the photoreceptor cells in the retina. 20/10 vision or better is possible even before additional magnification is considered. Further, it is possible for an electro-active lens to act as a telescope or as a microscope.

Fourth, electrical control creates the potential for changing the optical characteristics of the electro-active IOL as desired. For example, the desired optical characteristics may be determined after the IOL is surgically implanted in order to compensate for any changes that occur during surgery, or for that matter an error in calculating or estimating the post surgery refractive error. Similarly, the optical characteristics of the IOL may be varied over time to compensate for changes in the user's eye. For example, if the user has a degenerative disease that affects a portion of the retina, then it is possible to remotely cause the implanted electro-active IOL to create prismatic power or even change its prismatic power in order to shift the image to a portion of the retina that is undamaged. By way of example only, each month (or as needed) the image may be shifted to the remaining undamaged portion of the retina with the highest concentration of receptor cells. This change can be accomplished post-surgically and remotely (meaning without additional surgery).

Fifth, electrical control creates the potential for the user to automatically or instinctively control the focus. For example, contractions of the muscular ciliary body can be measured by an piezoelectric element (as a strain gauge), and these contractions can then be used as a control input to electrically adjust the focus of the IOL, similar to the way the ciliary body would focus the natural crystalline lens by physical deformation. Additionally, in theory, the focus could be controlled by electrical signals directly from the brain. Recent development with artificial limbs use this technique.

Sixth, electrical control creates the potential to shift the field of view, and thus compensate for diseases that prevent the eyeball from moving. Nervous signals to diseased muscles (that can no longer move the eye) may be intercepted, translated, and used to electrically shift the field of view.

Seventh, there are many types of electro-active element configurations. These configurations include: pixelated (typically a two dimensional array of pixels similar to a liquid crystal monitor on a computer), rotationally symmetric pixelated (for example, a set of concentric circles), and diffractive. Electro-active individually addressable pixelated diffractive lenses may use concentric ring shaped electrodes to product the diffractive lens power with varying index of refraction without physically machining, molding or etching diffractive elements into the surface of the lens.

The electro-active element may be used in combination with a conventional lens, wherein the conventional lens may provide a base refractive power. The electro-active element may be used in combination with a diffractive lens having a machined, molded, or etched surface or geometry. The electro-active element may be used in combination with a second electro-active element, wherein each may perform a different function. For example, the first electro-active element may provide focus, and the second may provide tinting or may serve as an electrically controlled aperture, or the second could cause a prismatic shift of the image to the healthy area of a retina of a deceased eye.

Eighth, as discussed above, it is possible to electrically replace many of the optical functions of a natural eye: tinting may replace or augment the light reducing effect of the contraction of the iris, focusing may replace the natural deformation of the crystalline lens, focusing and prismatic shifting may replace movement of the eyeball, and so forth. Among other factors, the present invention addresses: positioning the IOL, energy storage, energy recharging, power generation, control, steering of the line of site to a targeted region of the retina altering the refractive power of the eye, augmenting or replacing the accommodative power of the crystalline lens, remote tuning post surgery of the electro-active IOL. Tuning comprises altering the power of the IOL and/or altering the location of the focus on the retina of the IOL.

FIG. 1 displays the major anatomical components of a human eye. The major anatomical components are: conjunctiva 110, ciliary body 112, iris 114, aqueous humor 116, pupil 118, anterior chamber 120, crystalline lens 122, cornea 124, extraocular muscles 126, sclera 128, chorid 130, macula lutea 132, optic nerve 134, retina 136, and vitreous humor 138. Although a human eye is described, this invention is also applicable to non-human eyes such as horses or dogs.

As background, the optical components of the eye will be described in detail. Light entering the eye first enters the cornea 124. The cornea 124 is transparent and provides about 40 diopters of the approximately 60 diopters total refractive power of the eye. Light then passes through the pupil 118. The pupil 118 is an aperture, and is variable in diameter from 1 mm to at least 8 mm. This gives an aperture range in excess of f20-f2.5, and a ratio of 32:1 for the amount of light permitted to enter the eye. The iris 114 serves as an adjustable diaphragm creating a pupil 118. The light then passes through the crystalline lens 122. The crystalline lens 122 is a transparent, encapsulated, biconvex body which is attached circumferentially to the ciliary body 112. The crystalline lens 122 contributes about 17 diopters to the total refractive power of a relaxed eye. The refractive power of the crystalline lens 122 may be altered by contractions of the ciliary muscles in the ciliary body 112, which deform the crystalline lens 122 and alter its refractive power. The light then passes through the vitreous humor 138 and finally contacts the retina 136. The retina 136 is the sensory neural layer of the eyeball and may be considered as an outgrowth of the brain, and is connected to the brain through the optic nerve 134. Near the center of the retina 136, the macula lutea 132 contains a central region of highest visual sensitivity called the fovea centralis or foveola (see FIG. 7) with a diameter of approximately 0.4 mm where the visual resolution is the highest. The small diameter of the foveola is one of the reasons why the optical axes must be directed with great accuracy to achieve good vision.

Thus, the human eye has an adjustable diaphragm (iris 114) and an adjustable refractive power (due to the ciliary body 112 deforming the crystalline lens 124).

An IOL can be placed in one of three locations: in the anterior chamber 120, which is between the cornea 124 and the iris 114; or in the posterior chamber (not shown) which is between the iris 114 and the crystalline lens 122; or as a replacement for the crystalline lens 122.

Generally, if the crystalline lens is diseased or damaged, then an IOL may be used to replace the crystalline lens. This IOL replacement for the crystalline lens may be accommodative, or non-accomodative. Replacing the crystalline lens allows the IOL to be conveniently positioned inside of a clear bag-like capsule that previously held the natural crystalline lens, and also allows the possibility of retaining some variable focus capability through interaction with the muscular ciliary body which circumferentially surrounds the clear bag-like capsule. In other cases, the IOL is placed extra capsulary (without the bag-like capsule).

However, if the crystalline lens is still functional, then it may be preferable to leave the crystalline lens undisturbed and to place the electro-active IOL into either the posterior chamber or the anterior chamber 120 of the eye, or into the corneal tissue similar to the Small Diameter Corneal Inlay (SDCI) discussed above. In these embodiments, the electro-active IOL could, by way of example only, provide optical power to correct for conventional refractive errors, correct for non-conventional refractive errors, create a prismatic image shifting effect that moves the location of focus to a healthier area of the retina, and add a tint, as opposed to replacing the optical power of the otherwise healthy crystalline lens.

Conventional refractive error is defined as one or more of: myopia, hyperopia, pesbyopia, and regular astigmatism. Non-conventional (or higher order) refractive errors are defined as all other refractive errors or aberrations which are not conventional refractive error.

In many cases, the electro-active IOL may be used during cataract surgery when the existing crystalline lens is defective. In this case, the electro-active IOL will actually replace the removed defective existing crystalline lens, and may provide a range of electro-active optical correction including conventional and/or non-conventional refractive errors, as well as provide refractive power to make up for the lost optical power resulting from the removal of the crystalline lens. In addition, the electro-active IOL can provide for the ability to accommodate without any movement, translation or change in its surface geometry. This is accomplished by localized programmed changes in the index of refraction of the electro-active IOL.

The most common and advanced cataract surgery technique is phacoemulsification or "phaco." The surgeon first makes a small incision at the edge of the cornea and then creates an opening in the membrane that surrounds the cataract-damaged lens. This thin membrane is called the capsule. Next, a small ultrasonic probe is inserted through the opening in the cornea and capsule. The probe's vibrating tip breaks up or "emulsifies" the cloudy lens into tiny fragments that are suctioned out of the capsule by an attachment on the probe tip. After the lens is completely removed, the probe is withdrawn leaving only the clear (now empty) bag-like capsule, which may act as support for the intraocular lens (IOL).

Phacoemulsification allows cataract surgery to be performed through a very small incision in the cornea. Stitches are seldom needed to close this tiny entry, which means that there is less discomfort and quicker recovery of vision than with other surgical techniques. Small incisions generally do not change the curvature of the cornea (unlike larger incisions that were required with older surgical techniques). Small incisions for more rapid rehabilitation of vision and possibly less dependence on glasses for good distance vision.

After removal of the cataract-damaged lens, an artificial intraocular lens (IOL) may be implanted. The IOL may be produced from soft acrylic or solid medical-grade silicone. IOLs may be folded so they can be implanted with a small injector, which uses the same incision through which the phaco probe was inserted at the beginning of the procedure. As the IOL is implanted, it may be allowed to unfold and anchor itself behind the eye's pupil over the remaining clear capsule. The IOL(s) to be implanted may be selected based on power calculations made before surgery. In the case of the present invention, the electro-active IOL may also be selected based on the range of electro-active correction required, the type of any other ocular disease being treated, and any special needs of the patient.

In most cases, the electro-active element would contribute typically +2.5 Diopters, +2.75 Diopters, +3.0 Diopters, or +3.25 Diopters of optical power. The base lens portion (which the electro-active element is in optical communication) which would contribute most, if not all, of the approximately 17 Diopters normally provided by the crystalline lens, would be measured and selected prior to surgery. However, unlike a conventional IOL, an electro-active IOL allows for remote tuning of its optical power (for example, in case the calculations made prior to surgery are not optimum after surgery).

Figure 2A:
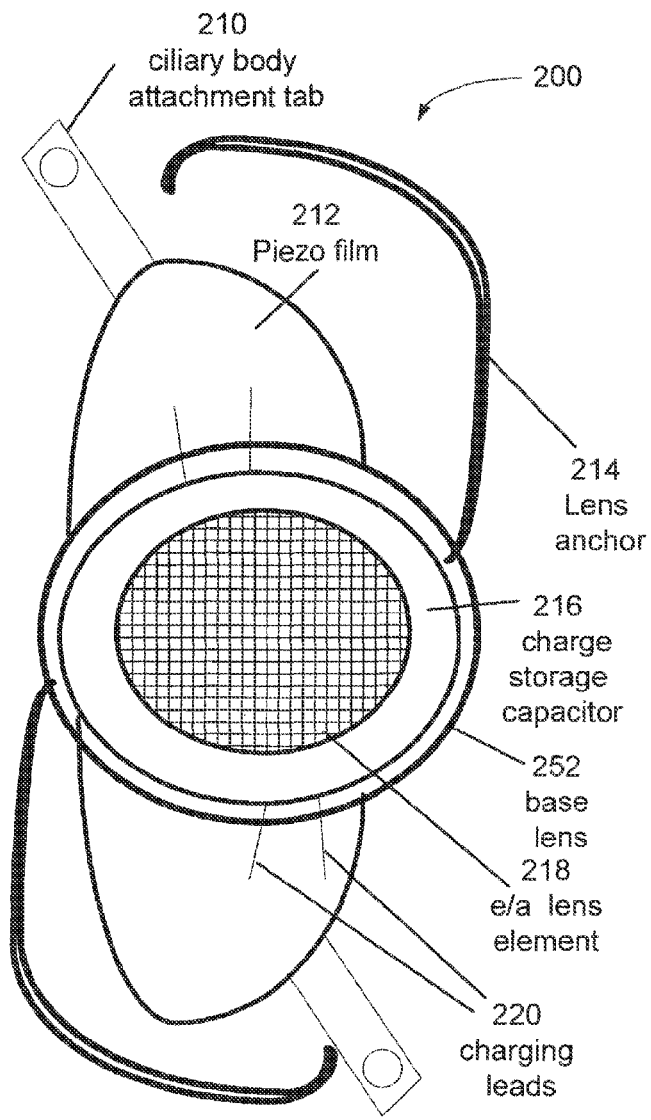
FIG. 2A displays a front view of an intraocular lens embodiment with an electro-active lens and piezoelectric material as a power supply.
Figure 2B:
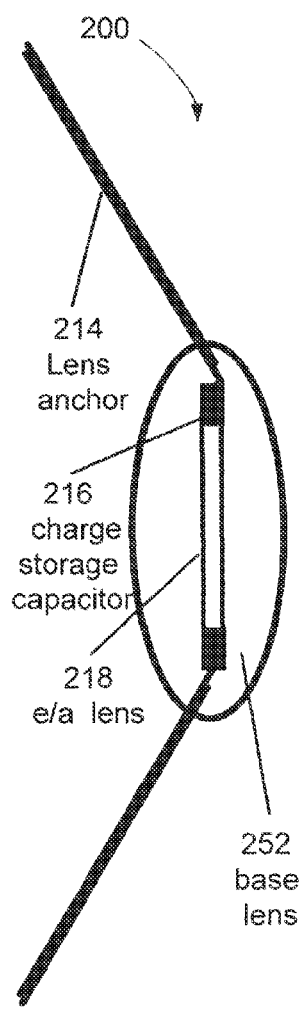
FIG. 2B displays a side view of an intraocular lens embodiment with an electro-active lens and piezoelectric material as a power supply.

FIGS. 2A and 2B illustrate an IOL assembly 200 according to an embodiment of the invention. FIG. 2A displays a front view of the IOL assembly, which includes an electro-active lens element 218 powered by a thin, annular charge storage capacitor 216 arranged around the perimeter of the electro-active lens element 218. The charge storage capacitor 216 is charged by a piezoelectric film 212. The piezoelectric film 212 generates this charge as a result of mechanical forces applied by the ciliary body (not shown). The piezoelectric film 212 is attached to the ciliary body by a ciliary body attachment tab 210.

The ciliary body expands and contracts as the eye attempts to focus from near to far and from far to near. The ciliary body movement may produce tension and/or compression of the piezoelectric film 212 which produces electricity. The electricity may be transferred through charging leads 220 and used to charge the charge storage capacitor 216 (or a rechargeable battery). The charge storage capacitor 216 may power the electro-active lens element 218 and any related control circuitry (not shown). Typically the electro-active lens element 218 requires approximately 1.0 to 5.0 volts, with a preferred range of 1.5 to 2.5 volts. These relatively low voltages decrease the risk involved with surgical placement of electrical devices.

The electrical characteristics of the piezoelectric film 212 under tension or compression may be used as a gauge to determine the desired viewing distance, and may be used to focus the electro-active lens. Thus, it is possible for the user to instinctively and automatically control the focus of the electro-active IOL 200 using the muscular ciliary body. The contractions of the muscular ciliary body previously focused the subject's crystalline lens by physically deforming it. Using the electro-active IOL 200 the instinctive and automatic contractions of the muscular ciliary body will change the electrical characteristics of the piezoelectric film 212, and these electrical changes may be monitored by a processor disposed, for example, on a chip (not shown) and used to electrically, variably focus the electro-active IOL 200. Alternatively, the piezoelectric film 212 may be used solely as a gauge for focusing, in which case, the electro-active IOL 200 would be provided with a different source of power.

In some embodiments, the piezoelectric film may be attached circumferentially to the ciliary body by multiple attachment tabs (more than two) in order to take advantage of the natural circumferential contraction and expansion of the surrounding ciliary body.

One or more lens anchors 214 may be used to stabilize the electro-active lens in the desired location. For example, a lens anchor 214 may be used to center the electro-active lens inside of the capsule or "bag" or membrane which formerly contained the natural crystalline lens (creating an intracapsular IOL). Alternately, the lens anchor 214 may be attached to the ciliary muscle directly, and thus be outside of the capsule (creating an extracapsular IOL).

Multiple lens anchors 214 may be used. For example, 3 or 4 lens anchors 214 may be used. The lens anchors 214 may have different shapes, customized to the specific application.

An optional base lens 252 may provide a base refractive power using a conventional lens configuration, and may be equivalent in refractive power to the crystalline lens when no accommodation is needed. The base lens 252 may also serve as a means of encapsulating the electro-active element in a hermetically sealed enclosure that consists of a biocompatible material similar to those materials currently used to make IOLs, by way of example only, soft acrylic or solid medical-grade silicone.

FIG. 2B displays a side view of an intraocular lens embodiment with an electro-active lens and piezoelectric material as a power supply. Specifically, FIG. 2B illustrates the optional base lens 252 which may surround the electro-active lens element 218 and which may provide a fixed or base refractive power. In a particular embodiment, the fixed or base refractive power may be adapted to focus the eye at near distances when the electro-active element is inactive. In another embodiment, the fixed or base lens may be adapted to focus the eye at far distances when the electro-active element is inactive. The optional base lens 252 may have multiple focal points, and/or may be tinted.

Other sources of power may include: solar cells, inductive charging, conductive charging, laser, thermo-electric, and harnessing the mechanical energy from blinking. The capacitor 216 (or optionally, a battery) may be recharged inductively with a pair of special glasses (spectacles) that may also remotely turn off the electro-active lens while the battery is being recharged. The special glasses may also be configured to provide vision correction while the battery is recharging.

Figure 5:
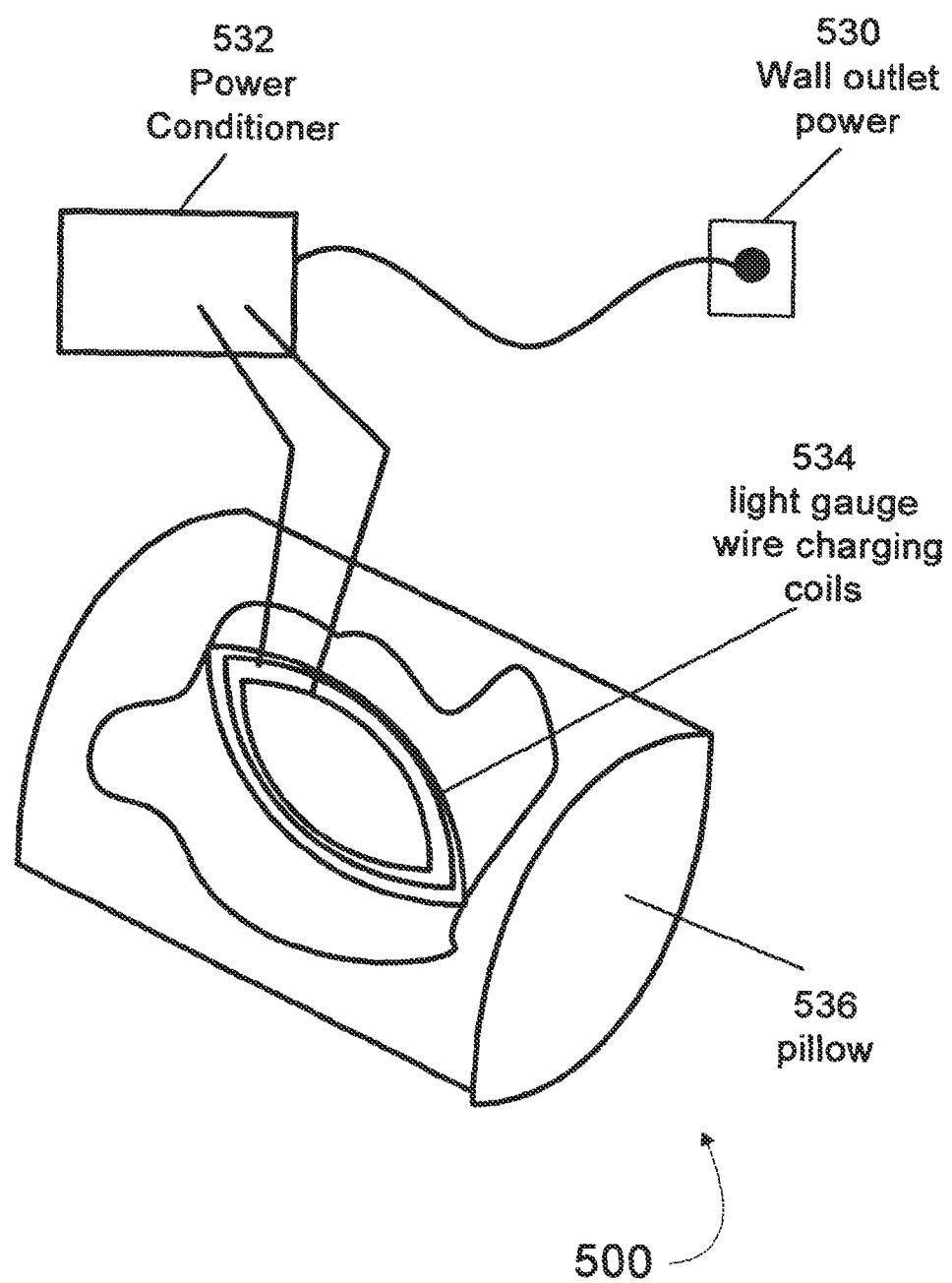
FIG. 5 displays an external power supply embodiment with inductive charging elements inside of a pillow.

In some embodiments, the capacitor 216 in the electro-active IOL 200 may be charged with a special pillow that has very light gauge wires through which current runs. The pillow may thus be used to charge the batteries inside the electro-active IOL 200 at night while the patient sleeps. An exemplary arrangement of this type is illustrated in FIG. 5 and will be discussed in more detail below. A power conditioning circuit is used to reduce the voltage and limit the current to safe levels for low power charging and to adjust the frequency for more efficient charging.

Alternately, the electro-active IOL may not have a capacitor 216 or battery, but may be constantly powered conductively by an externally located battery, or may be constantly powered inductively by an externally located inductively coupled power supply, or solar cell, or solar cell coupled to a properly tuned laser, or a thermal-electric power supply that generates electricity by dumping body heat (typically 98 degrees F.) into the relatively cool ambient air (typically 70 degrees F.).

Figures 3A, 3B:
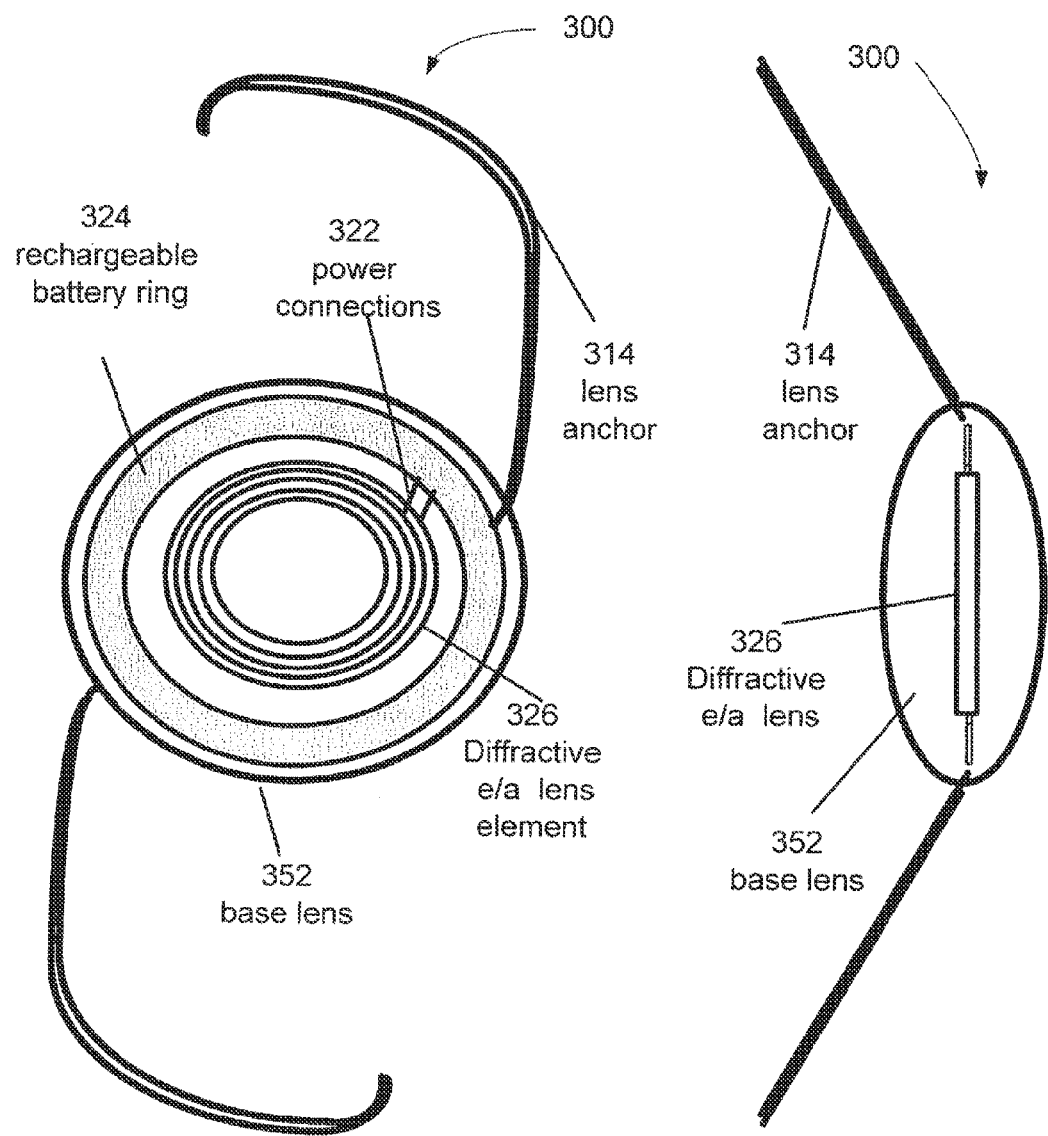
FIG. 3A displays a front view of an intraocular lens embodiment with a diffractive electro-active lens and a rechargeable battery ring.
FIG. 3B displays aside view of an intraocular lens embodiment with a diffractive electro-active lens and a rechargeable battery ring.

FIGS. 3A and 3B display an intraocular lens system 300 having a diffractive electro-active lens element 326 and a rechargeable battery ring 324. FIG. 3A provides a front view of the diffractive electro-active lens element 326, said diffractive lens element can be either electrically diffractive with circular concentric electrodes, or mechanically diffractive with etched surfaces that are activated electrically by controlled by index matching and mis-matching, which is connected by power connections 322 to the rechargeable battery ring 324. Lens anchors 314 may be used to stabilize and position the diffractive electro-active lens element 326 in the desired location and orientation. The rechargeable battery ring 324 may be powered with a capacitor similar to that of intraocular lens system 200 of FIGS. 2A and 2B. Further, the rechargeable battery 324 may be shaped differently and located inside of or adjacent the lens anchor 314, and thus be moved away from the optical elements.

FIG. 3B displays a side view of the intraocular lens 300. Specifically, FIG. 3B illustrates an optional base lens 352, which is similar to the base lens 252 of the intraocular lens system 200 of FIGS. 2A and 2B. This base lens 352 may have a base or fixed optical power, or may have no optical power and merely serve as a protective capsule or substrate.

FIGS. 4A and 4B display an intraocular lens system 400 having a pixelated electro-active lens element 430 and a rechargeable battery ring 424. FIG. 4A shows a front view of the pixelated electro-active lens element 430, which is connected by power connections 422 to the rechargeable battery ring 424. Lens anchors 414 may be used to stabilize and position the diffractive electro-active lens element 430 in the desired location and orientation. The rechargeable battery ring 424 may be powered in the same ways as capacitor 216 from FIG. 2.

FIG. 4B displays a side view of the intraocular lens 400 showing the base lens 452, which is similar to the base lenses of the previous embodiments.

FIG. 5 displays an external power supply 500 for use in charging the internal power supply of IOLs according to some embodiments of the inventions. In the power supply 500, a power conditioner 532 is electrically connected to a wall outlet 530. The power conditioner 532 is connected to light gauge wire induction coils 534 inside of a pillow 536 for inductively charging a capacitor or battery of a rechargeable electro-active IOL. The power conditioner 532 may be configured to reduce the voltage and limit the current to safe levels for low power charging and to adjust the frequency for more efficient charging. The power supply 500 may be configured so that the electro-active IOL may be charged while a subject rests his head on or near the pillow 536. It will be understood that the induction coils 534 may alternatively be placed in a subject's bedding or in a headrest, seatback or other location that can be in close proximity to a subjects head for a sufficient period of time.

Figure 6:
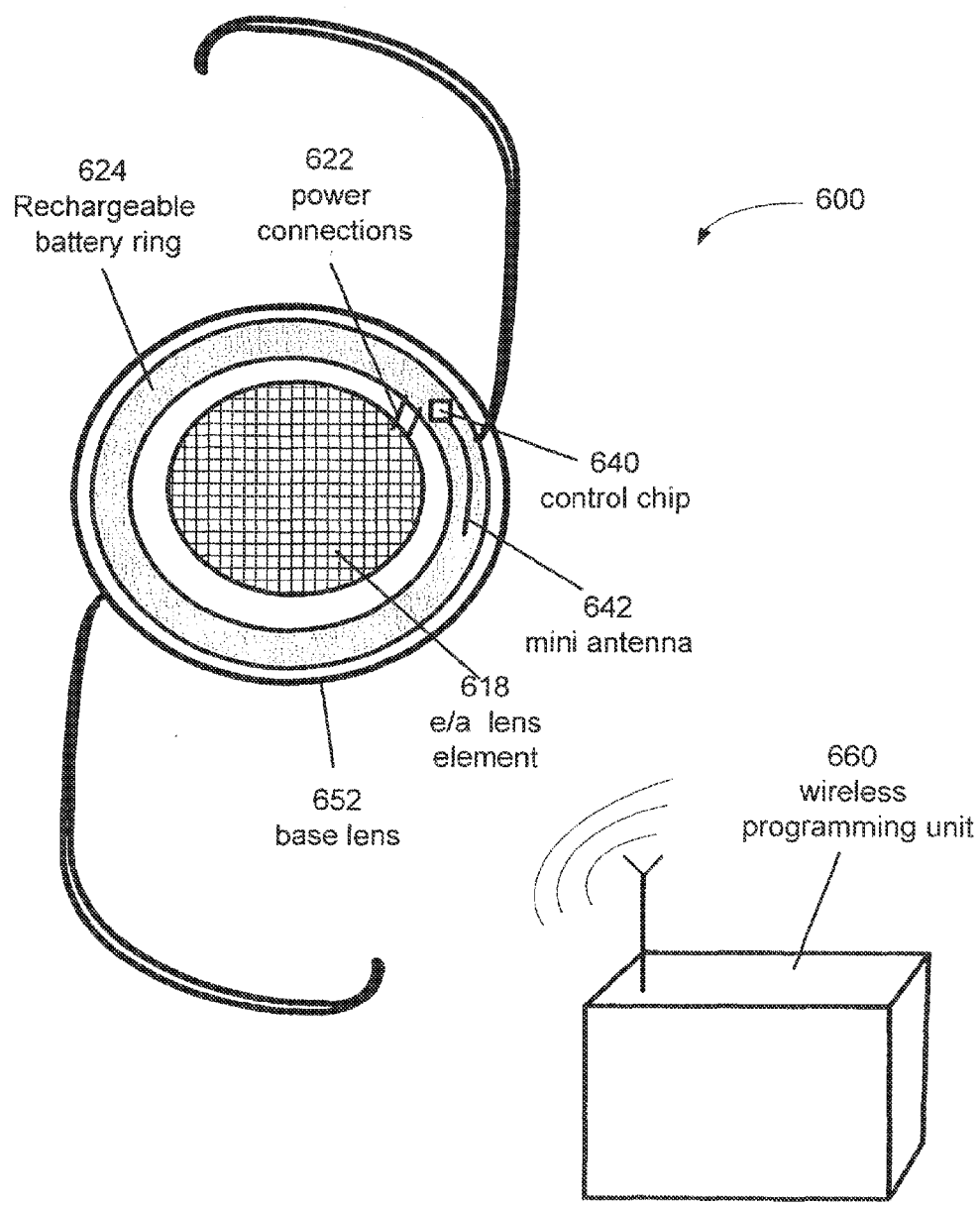
FIG. 6 displays an intraocular lens embodiment with an electro-active lens and a control chip with an antenna for use with a wireless programming unit.

FIG. 6 displays an intraocular lens assembly 600 with an electro-active lens element 618, a control chip 640 and an antenna 622 for use with a wireless programming unit 660. The wireless programming unit 660 is configured to communicate with the control chip 640 through radio waves. The radio waves are picked up by the mini antenna 642 which communicates with the control chip 640. The control chip 640 may be remotely tuned through the use of these radio waves. Such tuning may include setting or adjusting the optical characteristics of the electro-active lens element 618. The control chip 640 controls the electro-active lens element 618, and may have bi-directional communication with the wireless programming unit 660. For example, the control chip 640 may be configured to alert the wireless programming unit 660 that the battery 624 voltage is low. Alternately, programming communication with the control chip 640 may be through a laser (light waves), instead of through radio waves.

The electro-active lens element 618 may be connected by power connections 622 to a rechargeable battery ring 624 or a capacitor (not shown), and may be charged by induction coils or by piezoelectric elements as in previously described embodiments.

In some embodiments, the correction provided by the electro-active IOL may vary depending upon the needs of the patient and the desired results. In some embodiments the electro-active element may only provide correction for presbyopia. In some embodiments, the electo-active IOL may provide remote fine tuned conventional correction. In some embodiments, the electo-active IOL may provide higher order (non-conventional) aberration corrections, by way of example only, coma, spherical aberration, trefoil, and other higher order aberrations. In some embodiments the electro-active element may also adjust the position of the image on the retina, by way of creating a prismatic shift of the image electronically. When correcting for higher orders aberrations and or correcting a prismatic shift of where the image is located on the retina, the electro-active IOL may utilize a plurality of pixels. A prismatic shift of the image is very useful in patients having conditions, by way of example only, macula degeneration of the retina (which may include alterations in color due to disease or specific degeneration of the macula lutea), macula holes, retinal tears, and neurological abnormalities that cause scotomas or a loss of vision in particular segments of the visual pathway (such as blind or dark spots in the field of vision, and blurred vision). It should be pointed out that in each of the use embodiments above the inventive electro-active IOL can be tuned remotely post surgery to effect the optimized effect desired.

Figure 7A:
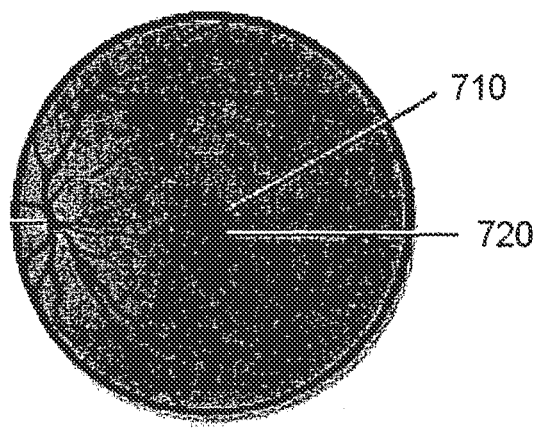
FIG. 7A is an image of an healthy retina illustrating the location of the macula and the fovea on the retina.
Figure 7B:
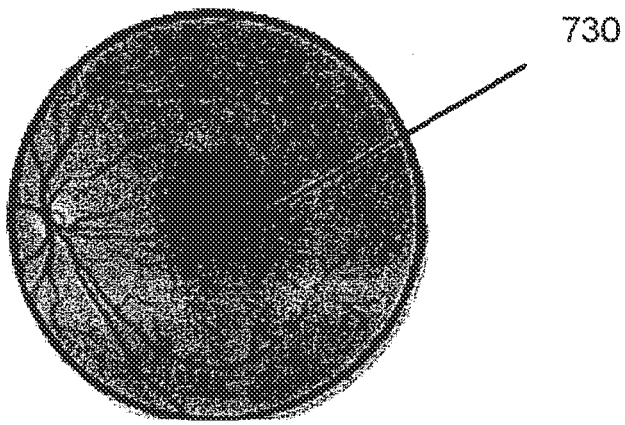
FIG. 7B illustrates an area of the macula that has been damaged by "wet" macular degeneration.
Figure 7C:
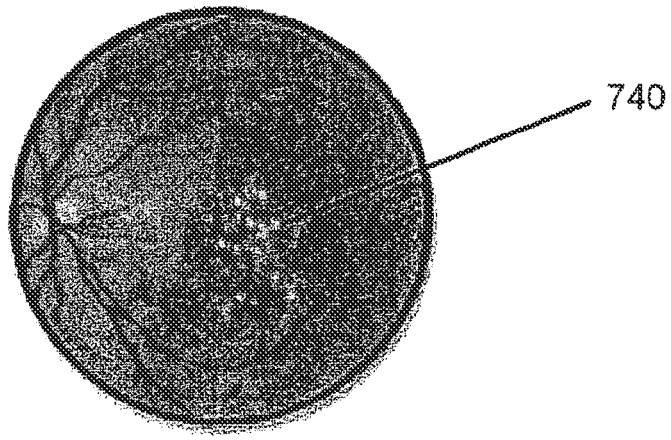
FIG. 7C illustrates an area of the macula that has been damaged by "dry" macular degeneration.

FIG. 7A illustrates an image of a healthy retina with a healthy fovea 720 and healthy macula 710. FIG. 7B illustrates an area of the macula 730 that has been damaged by "wet" macular degeneration, usually caused by bleeding from behind the retina that moves across membrane of the retina. FIG. 7C illustrates an area of the macula 740 that has been damaged by "dry" macula degeneration, which is caused by the build-up of drusen on the retina in the area of the macula. By moving the image to another location on the retina, vision can be improved for people suffering from macular degeneration. An image location change of 0.25 mm to 3.00 mm may make a major improvement in one's vision in the case of a diseased or damaged macula or retina. The preferred range is 0.50 mm to 2.00 mm.

Figure 8:
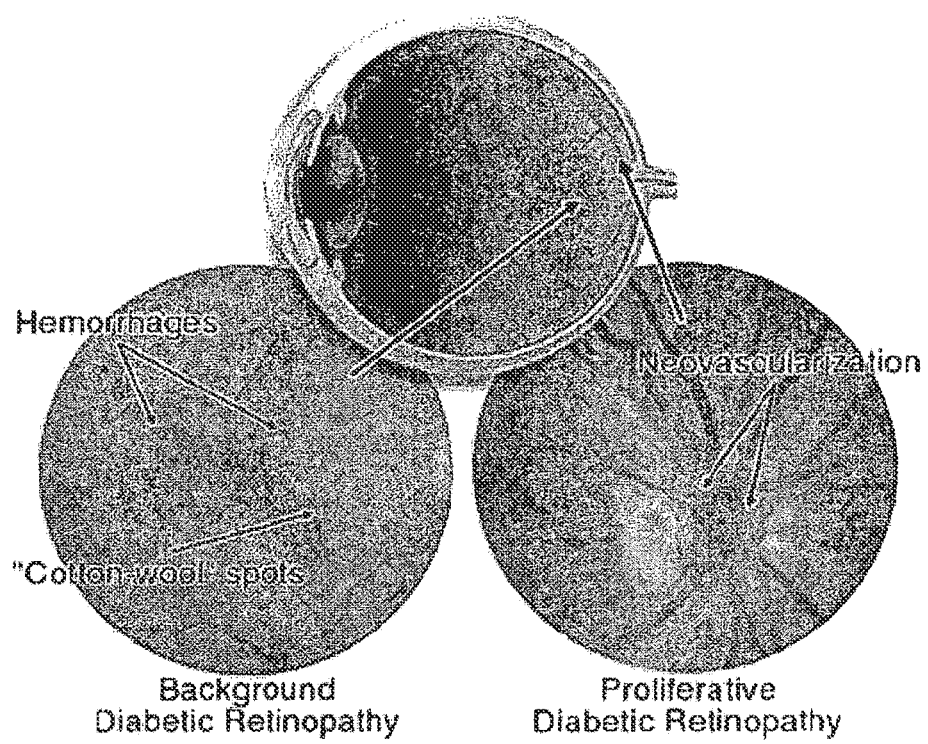
FIG. 8 illustrates the various manifestations of diabetic retinopathy.

FIG. 8 illustrates the effects of diabetic retinopathy on the eye. Again, by redirecting the image on the retina with a prismatic IOL, some of the visual clarity effects of this disease may be mitigated.

Figure 9:
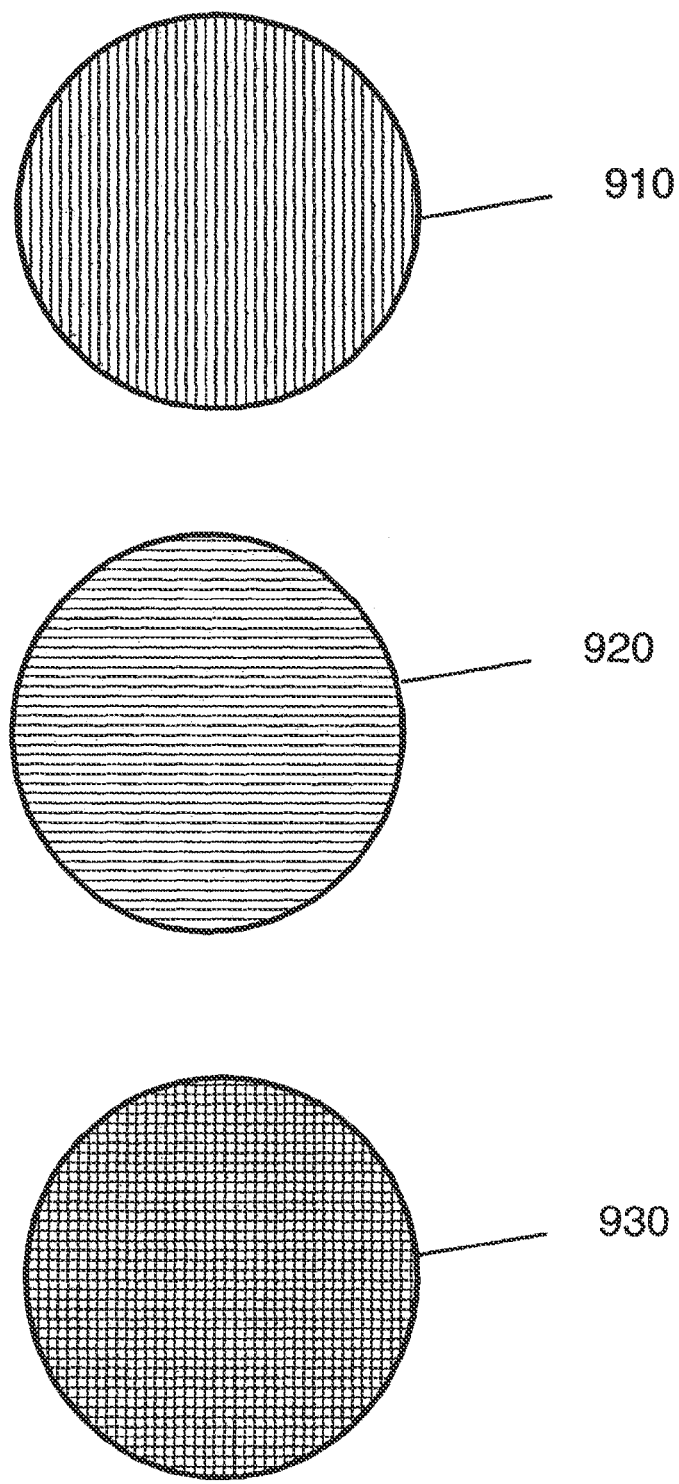
FIG. 9 illustrates the stacking of two prismatic lenses with linear electrodes to produce any combination of vertical and horizontal displacement of an image on the retina

FIG. 9 schematically illustrates an embodiment whereby electro-active lenses with linear electrodes may be stacked to produce any combination of vertical and horizontal displacement of an image on the retina. The first lens 910 has horizontal electrodes used to produce vertical prismatic power. The second lens 920 has vertical electrodes used to produce horizontal prismatic power. The combined lens 930 would be able to produce a combination of vertical and horizontal image displacement. By changing the voltages on each electrode and invoking a technique known as phase-wrapping, a variety of prismatic powers may be produced by such a lens. Also, multiple lenses may be stacked to produce larger values of prismatic power. The amount of prismatic power required and the resulting amount of image shift will vary depending upon the extent of the disease. A preferred range of image movement is between 0.1 mm and 3.0 mm, with a preferred range of 0.5 mm to 2.0 mm.

Figure 10:
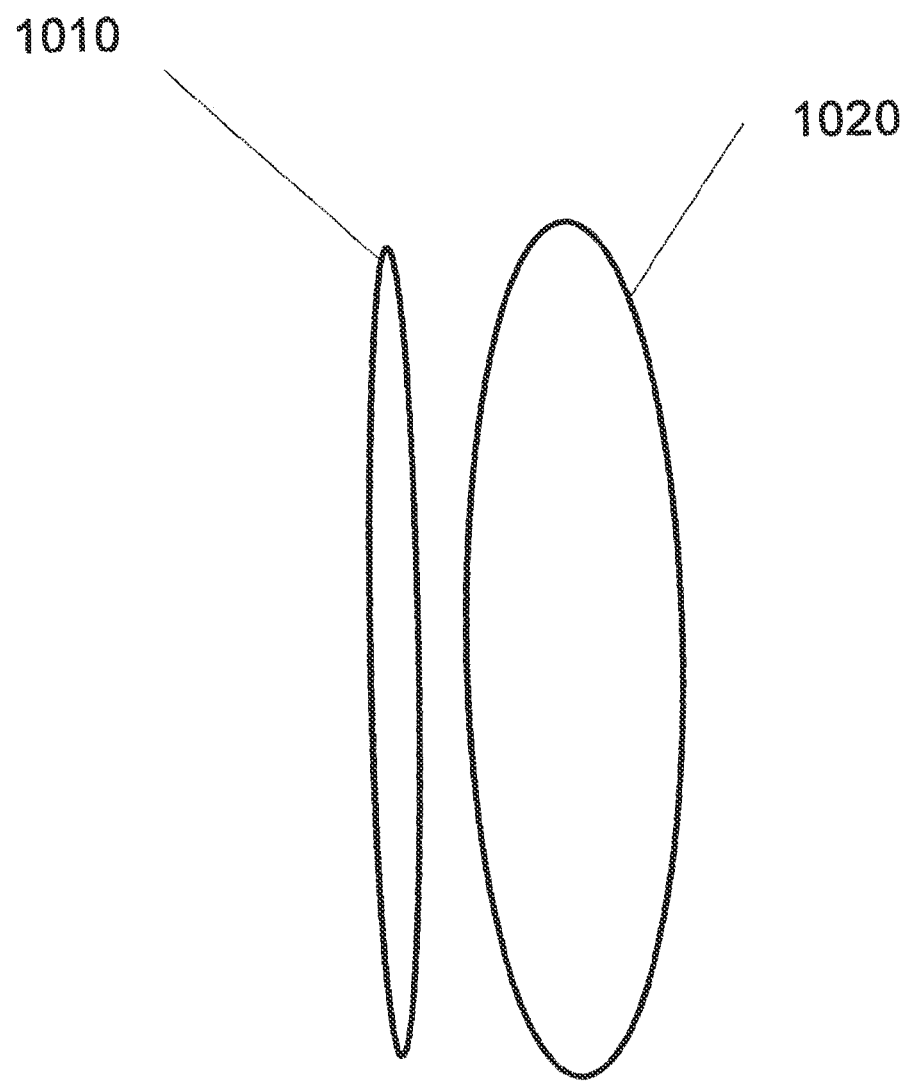
FIG. 10 illustrates an electro-active IOL in optical communication with a non-electro-active accommodative IOL.

FIG. 10 illustrates an electro-active IOL in optical communication with a non-electro-active accommodative IOL. Element 1010 is an electro-active lens that is in optical communication with non-electro-active accommodative IOL element 1020. Note that elements 1010 and 1020 are in optical series, but they are not physically touching each other.

While much consideration has been given to powering an electro-active lens, some electro-active materials retain their optical power in the absence of applied electricity (such, as by way of example only, a bi-stable liquid crystal). Using these type of electro-active materials, the prismatic power, an additive or subtractive power that is additive or subtractive to the base optical power of the IOL, and/or the higher order corrections could be set while the device is being powered, and then would remain set after the power is removed. This may negate the need for recharging the power source in the IOL. If the patient's vision changes and requires new correction, he could return to the eye-care professional and have the IOL adjusted to a new combination of prismatic and/or higher order correction. The changes could be externally powered remotely. For example, the external power may be RF energy similar to the way RFID tags work today, where the reading device provides the power to the RFID tag inductively so that the RFID can transmit it's information to the RFID reader.

In same manner as the RFID tags, a tuning instrument for changing the IOL power could provide power to the controller on the electro-active IOL, so that the controller could change the voltages on the electrodes of the IOL thus setting the localized index of refraction that determines the optical properties of the electro-active IOL.

Alternately, the power may also be supplied optically by shining a bright light or eye-safe laser into the eye and onto a photocell built into the electro-active IOL that would then provide the temporary electrical power needed to adjust the optical power of the electro-active IOL. This system may also be used for communication, in addition to supplying power.

Bi-stable twisted nematic, cholesteric and ferroelectric liquid crystals have been used in flexible low cost LCD displays, and similar materials may be used in the electro-active elements of an IOL. This type of electrically adjusted (but otherwise non-powered) prismatic adjustment, additive or subtractive, for retinal disease tuning or higher order aberration correction may be added to (i.e., placed in optical series with) any accommodative non electro-active IOL that corrects for presbyopia. For example, electro-active elements could be placed in optical series with non-electrical or non-powered IOLs, such as non electro-active IOLs that mechanically change their optical power by changing one or more surface curvatures and/or the position of the IOL in the eye.

The addition of the electro-active lens or electro-active elements may be accomplished in at least three ways: first, a separate electro-active IOL may be placed in non-touching optical communication (optical series) with the non-electro-active accommodating IOL; second, an electro-active element can be built into one of the IOL's surfaces that does not change contour during accommodation; and third, an electro-active element may be placed inside of a layered non-electro-active.

For example, an electro-active element could be added in the anterior chamber and used in optical series with an individual's functioning crystalline lens. In this case, the crystalline lens will provide natural accommodation, and the electro-active IOL may steer the image to a healthier part of the retina, or may tune the non-electroactive IOL, or may correct for higher order aberration.

As noted above, in some embodiments, it may be a major advantage to tune or adjust the electro-active IOL remotely. After inserting the electro-active IOL in the eye, the optical power and the prismatic power can be fine-tuned remotely to accomplish the optimal vision correction to correct for conventional refractive error, or higher order aberrations, or the precise location of the image on the retina. Further, the IOL could be tuned again at a later date to compensate for changes in the eye over time, due to disease or aging. In cases of correcting solely for conventional refractive error, the electro-active IOL could either utilize diffraction or pixelation or both. The electro-active element may also perform any number of these functions in combination, as required by the patient's conditions and at the discretion of the eye care professional.

In some embodiments, while an electro-active lens may be used to provide vision correction as described in the present invention, the electro-active lens may also be used to provide a sunglass or tinting effect electro-actively. By using special liquid crystal layers or other electro-chromic materials, the electro-active IOL of the present invention can reduce the amount of light that hits the retina when the light levels in the environment become uncomfortably high, or reach a level that can be dangerous to the eye. The sunglass effect may be triggered automatically when a light sensor built into the IOL receives an intensity of light beyond some threshold level. Alternately, the sunglass effect may be switched remotely by the user using a wireless communication device couple to the control circuitry in the IOL. This electro-active sunglass effect may occur in milliseconds or less, in contrast to the relatively slow reaction time of seconds (or more) for commercial photosensitive chemical tints in conventional lenses. One factor in determining the reaction time of electro-active lenses is the thinness of the liquid crystal layer. For example, a 5 micron layer of liquid crystal may react in milliseconds.

Similarly, the focusing of the electro-active elements may be performed automatically by using a range finder, or a tilt meter (near distance when looking down, far distance when looking straight), or may be controlled remotely by the user using a wireless communication device.

There are a number of electro-chromic materials. One type consists of transparent outside layers of electrically conductive film that has inner layers which allow the exchange of ions. When a voltage is applied across the outer conductive layers, ions move from one inner layer to another, causing a change in tinting of the electro chromic material. Reversing the voltage causes the layer to become clear again. The electro-chromic layers can have variable light transmittance during operation, from about 5 to 80 percent. This type of electro chromic glazing has "memory" and does not need constant voltage after the change has been initiated. Further, it can be tuned to block certain wavelengths, such as infrared (heat) energy.

Another electro-chromic technology is called suspended particle display (SPD). This material contains molecular particles suspended in a solution between the plates of glass. In their natural state, the particles move randomly and collide, blocking the direct passage of light. When switched on, the particles align rapidly and the glazing becomes transparent. This type of switchable glazing can block up to about 90 percent of light. Also liquid crystal has been used to provide electro-chromic effects in sunglasses.

The systems and methods, as disclosed herein, are directed to the problems stated above, as well as other problems that are present in conventional techniques. Any description of various products, methods, or apparatus and their attendant disadvantages described in the "Background of the Invention" is in no way intended to limit the scope of the invention, or to imply that invention des not include some or all of the various elements of known products, methods and apparatus in one form or another. Indeed, various embodiments of the invention may be capable of overcoming some of the disadvantages noted in the "Background of the Invention," while still retaining some or all of the various elements of known products, methods, and apparatus in one form or another.

What is claimed:

1. An implantable ophthalmic device to be implanted in an eye of a subject, the implantable ophthalmic device comprising:
   a bi-stable electro-active element to provide a first optical power in a first state and a second optical power in a second state;
   a controller, operably coupled to the bi-stable electro-active element, to apply electrical power to the bi-stable electro-active element so as to switch the bi-stable electro-active element between the first state and the second state and to remove the electrical power from the bi-stable electro-active element after switching the bi-stable electro-active element between the first state and the second state; and
   a conductive coil, in electrical communication with the controller, to receive the electrical power via wireless charging and to provide the electrical power to the controller.

2. The implantable ophthalmic device of claim 1, wherein the bi-stable electro-active element comprises a bi-stable liquid crystal material to provide a refractive index change in response to the electrical power applied by the controller.

3. The implantable ophthalmic device of claim 1, wherein the bi-stable electro-active element comprises a plurality of independently controllable pixels.

4. The implantable ophthalmic device of claim 1, wherein, in the second state, the bi-stable electro-active element is configured to provide at least partial correction for at least one higher-order aberration of the eye.

5. The implantable ophthalmic device of claim 1, wherein, in the second state, the bi-stable electro-active element is configured to provide compensation for at least one change in the subject's vision.

6. The implantable ophthalmic device of claim 1, wherein the controller is configured to switch the bi-stable electro-active element between the first state and the second state in response to a control signal received via the conductive coil, from an apparatus external to the eye.

7. The implantable ophthalmic device of claim 6, wherein the wireless receiver is configured to receive at least a portion of the electrical power applied by the controller to the electro-active element between the first state and the second state from the apparatus external to the eye.

8. The implantable ophthalmic device of claim 6, wherein the second optical power is selected to compensate for a change in the subject's vision after implantation of the implantable ophthalmic device.

9. A method of adjusting an implantable ophthalmic device comprising a bi-stable electro-active element, implanted in an eye, that provides a first optical power in a first state and a second optical power in a second state, the method comprising:
   receiving electrical power at a conductive coil in the implantable ophthalmic device via wireless charging;
   applying the electrical power to the bi-stable electro-active element so as to switch the bi-stable electro-active element from the first state and the second state; and
   removing the electrical power from the bi-stable electro-active element after switching the bi-stable electro-active element from the first state and the second state.

10. The method of claim 9, wherein applying the electrical power to the bi-stable electro-active element causes a change in a refractive index of the bi-stable electro-active element.

11. The method of claim 9, wherein applying the electrical power to the bi-stable electro-active element comprises selectively applying electrical power to one or more independently controllable pixels in the bi-stable electro-active element.

12. The method of claim 9, further comprising, in the second state:

providing at least partial correction for at least one higher-order aberration of the eye.

13. The method of claim 9, further comprising, in the second state:
providing compensation for at least one change in the subject's vision.

14. The method of claim 9, further comprising:
receiving a control signal via the conductive coil from an apparatus external to the eye; and
applying the electrical power to the bi-stable electro-active element in response to the control signal.

15. The method of claim 14, wherein the second optical power is selected to compensate for a change in the subject's vision after implantation of the implantable ophthalmic device.

16. An implantable ophthalmic device to be implanted in an eye of a subject, the implantable ophthalmic device comprising:
a static optical element to provide a fixed optical power;
a bi-stable electro-active element, in optical communication with the static optical element, to provide a variable optical power that at least partially corrects for a higher-order aberration in the eye and/or a change in the subject's vision;
a controller, operably coupled to the electro-active element, to apply electrical power to the bi-stable electro-active element in response to a control signal so as to change the variable optical power of the bi-stable electro-active element and to remove the electrical power from the bi-stable electro-active element after changing the variable optical power of the bi-stable electro-active element; and
a wireless receiver, operably coupled to the controller, to receive the control signal and at least a portion of the electrical power applied to the bi-stable electro-active element from a tuning apparatus external to the eye.

17. The implantable ophthalmic device of claim 16, wherein the bi-stable electro-active element is further configured to provide a change in transmittance in response to the electrical power applied by the controller.

* * * * *